US007084294B2

(12) United States Patent
Jungkamp et al.

(10) Patent No.: US 7,084,294 B2
(45) Date of Patent: Aug. 1, 2006

(54) METHOD FOR THE RECYCLING OF A LEWIS ACID

(75) Inventors: Tim Jungkamp, Sandhausen (DE); Jens Scheidel, Hirschberg (DE); Hermann Luyken, Ludwigshafen (DE); Michael Bartsch, Neustadt (DE); Robert Baumann, Mannheim (DE); Gerd Haderlein, Grünstadt (DE)

(73) Assignee: BASF Aktiengesellschaft (DE)

( * ) Notice: Subject to any disclaimer, the term of this patent is extended or adjusted under 35 U.S.C. 154(b) by 58 days.

(21) Appl. No.: 10/520,007

(22) PCT Filed: Jul. 4, 2003

(86) PCT No.: PCT/EP03/07150

§ 371 (c)(1), (2), (4) Date: Dec. 30, 2004

(87) PCT Pub. No.: WO2004/007431

PCT Pub. Date: Jan. 22, 2004

(65) Prior Publication Data

US 2005/0247624 A1 Nov. 10, 2005

(30) Foreign Application Priority Data

Jul. 10, 2002 (DE) ................................ 102 31 292
Aug. 27, 2002 (DE) ................................ 102 40 012

(51) Int. Cl.
*C07C 253/10* (2006.01)

(52) U.S. Cl. ...................................................... 558/338

(58) Field of Classification Search ................. 558/338
See application file for complete search history.

(56) References Cited

U.S. PATENT DOCUMENTS 3,773,809 A 11/1973 Walter et al.
4,082,811 A * 4/1978 Shook, Jr. ...................... 568/1
4,082,881 A 4/1978 Chen et al.
4,705,881 A 11/1987 Rapoport
6,048,996 A 4/2000 Clarkson et al.
6,127,567 A 10/2000 Garner et al.
6,171,996 B1 1/2001 Garner et al.
6,380,421 B1 4/2002 Lu et al.
2002/0022736 A1 2/2002 Burattin et al.

FOREIGN PATENT DOCUMENTS

EP 0 417 325 A1 3/1991
WO WO 96/33969 10/1996

OTHER PUBLICATIONS

International Search Report for International Application No. PCT/EP 03/07150.

* cited by examiner

*Primary Examiner*—Kamal A. Saeed
*Assistant Examiner*—Joseph R. Kosack
(74) *Attorney, Agent, or Firm*—Connolly, Bove, Lodge & Hutz, LLP

(57) ABSTRACT

A process for the recovery of a Lewis acid from a reaction mixture (I) which has been obtained in the hydrocyanation of an olefinically unsaturated compound to a nitrile which has a miscibility gap with water under certain pressure and temperature conditions, in the presence of a catalyst system comprising a Lewis acid and a complex compound. The method comprises a) removing the complex compound from mixture (I) to give a mixture (II), b) adding water to mixture (II) and placing mixture (II) under pressure and temperature conditions to provide a phase (III) and a phase (IV), c) adding a liquid diluent (V) which c1) does not form an azeotrope with water and whose boiling point under certain pressure conditions is higher than that of water, or c2) forms an azeotrope or heteroazeotrope with water under certain pressure conditions, to phase (III), d) subjecting the mixture of phase (III) and liquid diluent (V) to distillation under the pressure conditions mentioned in step c1) or c2), and e) subjecting mixture (VII) to hydrocyanation of an olefinically unsaturated compound to give the nitrile.

18 Claims, No Drawings

METHOD FOR THE RECYCLING OF A LEWIS ACID

CROSS REFERENCE TO RELATED APPLICATION

The present application is a National Phase application of PCT/EP2003/07150, filed Jul. 4, 2003, which claims priority from Germany Patent Application No. DE 102 31 292.3, filed Jul. 10, 2002 and Germany Patent Application No. DE 102 40 012.1, filed Aug. 27, 2002.

The present invention relates to a process for the recovery of a Lewis acid from a reaction mixture (I) which has been obtained in the hydrocyanation of an olefinically unsaturated compound to a nitrile which has a miscibility gap with water under certain amount, pressure and temperature conditions, in the presence of a catalyst system comprising a Lewis acid and a complex compound comprising a phosphorus-containing compound which is suitable as ligand and a central atom which is suitable for this compound, which comprises a) removing the said complex compound from mixture (I) to give a mixture (II), b) adding water to mixture (II) and placing the latter under pressure and temperature conditions such that a phase (III) which has a higher content of water than of the said nitrile and a phase (IV) which has a higher content of the said nitrile than of water are obtained, where phase (III) has a higher content of the said Lewis acid than does phase (IV), c) adding a liquid diluent (V) which c1) does not form an azeotrope with water and whose boiling point under certain pressure conditions is higher than that of water or c2) forms an azeotrope or heteroazeotrope with water under certain pressure conditions, to phase (III), d) subjecting the mixture of phase (III) and liquid diluent (V) to distillation under the pressure conditions mentioned in step c1) or c2), giving a mixture (VI) which has a higher content of water than of diluent (V) and a mixture (VII) which has a higher content of diluent (V) than of water, where mixture (VII) has a higher content of the said Lewis acid than does mixture (VI), and e) subjecting mixture (VII) to hydrocyanation of an olefinically unsaturated compound to give a nitrile which has a miscibility gap with water under certain amount, pressure and temperature conditions, in the presence of a catalyst system comprising a Lewis acid and a complex compound comprising a phosphorus-containing compound which is suitable as ligand and a central atom which is suitable for this compound.

Processes are known for the hydrocyanation of olefinically unsaturated compounds to give a nitrile which has a miscibility gap with water under certain amount, pressure and temperature conditions, in the presence of a catalyst system comprising a Lewis acid and a complex compound comprising a phosphorus-containing compound which is suitable as ligand and a central atom which is suitable for this compound.

Thus, U.S. Pat. Nos. 4,705,881, 6,127,567, 6,171,996 B1 and 6,380,421 B1 disclose processes for the hydrocyanation of pentenenitrile to adiponitrile in the presence of a catalyst system comprising a Lewis acid and a complex compound which contains a multidentate phosphite ligand and nickel as central atom.

U.S. Pat. No. 4,082,811 describes the removal of triphenylboron from a reaction mixture of this type by precipitation as the $NH_3$ adduct. This process has the disadvantage that the Lewis acid can only be liberated from the precipitate in a complex manner and in addition the recovery of the catalyst system from the filtrate is made more difficult by complex formation of the nickel with the ammonia employed.

It is an object of the present invention to provide a process which enables the recovery of the Lewis acid from a reaction mixture of this type in a form which enables re-use of the Lewis acid in the said hydrocyanation, in a technically simple and economical manner.

We have found that this object is achieved by the process defined at the outset.

The process according to the invention furthermore has the advantage that it enables the complex compound comprising a phosphorus-containing compound which is suitable as ligand and a central atom which is suitable for this compound that is employed as constituent of the catalyst system to be removed in a form which enables re-use of the complex compound in the said hydrocyanation and also enables the target product obtained in the hydrocyanation to be removed from the reaction mixture obtained in the hydrocyanation in a technically simple and economical manner.

In step a) of the process according to the invention, use is made of a reaction mixture (I) which has been obtained in the hydrocyanation of an olefinically unsaturated compound to a nitrile which has a miscibility gap with water under certain amount, pressure and temperature conditions, in the presence of a catalyst system comprising a Lewis acid and a complex compound comprising a phosphorus-containing compound which is suitable as ligand and a central atom which is suitable for this compound.

In a preferred embodiment, a suitable nitrile which has a miscibility gap with water under certain amount, pressure and temperature conditions is adiponitrile.

Processes for the preparation of adiponitrile by hydrocyanation of an olefinically unsaturated compound, such as 2-cis-pentenenitrile, 2-trans-pentenenitrile, 3-cis-pentenenitrile, 3-trans-pentenenitrile, 4-pentenenitrile, E-2-methyl-2-butenenitrile, Z-2-methyl-2-butenenitrile, 2-methyl-3-butenenitrile or a mixture thereof, in the presence of a catalyst system comprising a Lewis acid and a complex compound containing a phosphorus-containing compound which is suitable as ligand, such as a monodentate, preferably multidentate, in particular bidentate compound, which is coordinated to a central atom via a phosphorus atom, which may be in the form of a phosphine, phosphite, phosphonite or phosphinite or a mixture thereof, and a central atom, preferably nickel, cobalt or palladium, in particular nickel, particularly preferably in the form of nickel(0), are known, for example from U.S. Pat. Nos. 4,705,881, U.S. 6,127,567, U.S. 6,171,996 B1 and U.S. 6,380,421 B1.

Suitable Lewis acids here are inorganic or organic metal compounds in which the cation is selected from the group consisting of scandium, titanium, vanadium, chromium, manganese, iron, cobalt, copper, zinc, boron, aluminum, yttrium, zirconium, niobium, molybdenum, cadmium, rhenium and tin. Examples include $ZnBr_2$, $ZnI_2$, $ZnCl_2$, $ZnSO_4$, $CuCl_2$, CuCl, $Cu(O_3SCF_3)_2$, $CoCl_2$, $CoI_2$, $FeI_2$, $FeCl_3$, $FeCl_2$, $FeCl_2(THF)_2$, $TiCl_4(THF)_2$, $TiCl_4$, $TiCl_3$, ClTi(O-i-propyl)$_3$, $MnCl_2$, $ScCl_3$, $AlCl_3$, $(C_8H_{17})AlCl_2$, $(C_8H_{17})_2AlCl$, $(i\text{-}C_4H_9)_2AlCl$, $(C_6H_5)_2AlCl$, $(C_6H_5)AlCl_2$, $ReCl_5$, $ZrCl_4$, $NbCl_5$, $VCl_3$, $CrCl_2$, $MOCl_5$, $YCl_3$, $CdCl_2$, $LaCl_3$, $Er(O_3SCF_3)_3$, $Yb(O_2CCF_3)_3$, $SmCl_3$, $B(C_6H_5)_3$ and $TaCl_5$, as described, for example, in U.S. Pat. Nos. 6,127,567, U.S.

6,171,996 and U.S. 6,380,421. Also suitable are metal salts, such as $ZnCl_2$, $CoI_2$ and $SnCl_2$, and organometallic compounds, such as $RAlCl_2$, $RSnO_3SCF_3$ and $R_3B$, where R is an alkyl or aryl group, as described, for example, in U.S. Pat. Nos. 3,496,217, U.S. 3,496,218 and U.S. 4,774,353. It is also possible to employ as promoter, in accordance with U.S. Pat. No. 3,773,809, a metal in cationic form selected from the group consisting of zinc, cadmium, beryllium, aluminum, gallium, indium, thallium, titanium, zirconium, hafnium, erbium, germanium, tin, vanadium, niobium, scandium, chromium, molybdenum, tungsten, manganese, rhenium, palladium, thorium, iron and cobalt, preferably zinc, cadmium, titanium, tin, chromium, iron and cobalt, where the anionic moiety can be selected from the group consisting of halides, such as fluoride, chloride, bromide and iodide, anions of lower fatty acids having from 2 to 7 carbon atoms, $HPO_3^{2-}$, $H_3PO^{2-}$, $CF_3COO^-$, $C_7H_{15}OSO_2^-$ or $SO_4^{2-}$. U.S. Pat. No. 3,773,809 furthermore discloses as suitable promoters borohydrides, organoborohydrides and borates of the formula $R_3B$ or $B(OR)_3$, where R is selected from the group consisting of hydrogen, aryl radicals having between 6 and 18 carbon atoms, aryl radicals which are substituted by alkyl groups having from 1 to 7 carbon atoms, and aryl radicals which are substituted by cyano-substituted alkyl groups having from 1 to 7 carbon atoms, advantageously triphenylboron. It is furthermore possible, as described in U.S. Pat. No. 4,874,884, to employ synergistically active combinations of Lewis acids in order to increase the activity of the catalyst system. Suitable promoters can be selected, for example, from the group consisting of $CdCl_2$, $FeCl_2$, $ZnCl_2$, $B(C_6H_5)_3$ and $(C_6H_5)_3SnX$, where $X{=}CF_3SO_3$, $CH_3C_6H_4SO_3$ or $(C_6H_5)_3BCN$, where the ratio between promoter and nickel is preferably in the range from about 1:16 to about 50:1.

For the purposes of the present invention, the term Lewis acid also covers the promoters mentioned in U.S. Pat. No. 3,496,217, U.S. Pat. No. 3,496,218, U.S. Pat. No. 4,774,353, U.S. Pat. No. 4,874,884, U.S. Pat. No. 6,127,567, U.S. Pat. No. 6,171,996 and U.S. Pat. No. 6,380,421.

Of the Lewis acids mentioned, particular preference is given, in particular, to metal salts, particularly preferably metal halides, such as fluorides, chlorides,. bromides and iodides, in particular chlorides, of which zinc chloride, iron(II) chloride and iron(III) chloride are particularly preferred.

The preparation of reaction mixtures (I) is known per se, for example from U.S. Pat. No. 3,496,217, U.S. Pat. No. 3,496,218, U.S. Pat. No. 4,774,353, U.S. Pat. No. 4,874,884, U.S. Pat. No. 6,127,567, U.S. Pat. No. 6,171,996 and U.S. Pat. No. 6,380,421.

In step a) of the process according to the invention, the said complex compound is separated off from mixture (I) to give a mixture (II).

This separation can be carried out in a manner known per se, preferably by extraction, as described, for example, in U.S. Pat. No. 3,773,809.

Suitable extractants are preferably alkanes or cycloalkanes. Alkanes which can be employed are advantageously n-pentane, n-hexane, n-heptane, n-octane and branched isomers thereof, or mixtures thereof, in particular those having a boiling point in the range from about 30 to about 135° C. Suitable cycloalkanes are advantageously cyclopentane, cyclohexane, cycloheptane and alkyl-substituted cycloalkanes, and mixtures thereof, in particular those having a boiling point in the range from about 30 to about 135° C., such as methylcyclohexane.

The extraction can advantageously be carried out at a temperature in the range from about 0 to about 100° C.

The extraction can be carried out batchwise or continuously, the continuous countercurrent procedure having proven advantageous.

The weight ratio between the phosphorus compound employed as ligand and the nitrile to be extracted should be in the range from 1:1000 to 90:100. The weight ratio between the extractant and the phosphorus compound which is suitable as ligand should advantageously be in the range from 2:1 to 100:1.

The extraction can be carried out under ambient pressure or under superatmospheric pressure in order to avoid evaporation of the extractant.

The complex compound can be isolated from the extract by removal of the extractant, for example by evaporation of the extractant, and, if desired, fed back into the hydrocyanation, as described in U.S. Pat. No. 3,773,809.

The mixture (II) obtained in step a) comprises the nitrile which has been obtained by hydrocyanation of an olefinically unsaturated compound and which has a miscibility gap with water under certain amount, pressure and temperature conditions, the Lewis acid used as constituent of the catalyst system employed for the hydrocyanation, and any by-products formed in the hydrocyanation, which may be dissolved in mixture (II) or are undissolved; the content of the complex compound comprising a phosphorus-containing compound which is suitable as ligand and a central atom which is suitable for this compound that is used as constituent of the catalyst system employed for the hydrocyanation is preferably from 0 to 60% by weight, in particular from 0 to 50% by weight, based on the total weight of mixture (I).

If mixture (II) comprises undissolved constituents, some or preferably all of these undissolved constituents can advantageously be removed from mixture (II) between steps a) and b) or between steps b) and c) of the process according to the invention; this separation can be carried out by methods known per se, for example by filtration or sedimentation.

The optimum apparatuses and process conditions for a separation of this type can easily be determined by means of a few simple preliminary experiments.

In accordance with the invention, water is added to mixture (II) in step b), and the system is placed under pressure and temperature conditions such that a phase (II) which has a higher content of water than of said nitrile and a phase (IV) which has a higher content of the said nitrile than of water is obtained, where phase (III) has a higher content of the said Lewis acid than does phase (IV).

The amount ratio of water to mixture (II) is not crucial per se. With increasing ratio of Lewis acid to be recovered in mixture (II) to water, the viscosity of phase (III) increases significantly, with the consequence that handling of the system comprising phase (IV) and phase (III) becomes increasingly difficult.

An amount of water such that a proportion of the Lewis acid in the region of at least 0.01% by weight, preferably at least 0.1% by weight, particularly preferably at least 0.25% by weight, especially preferably at least 0.5% by weight, based on the total weight of phase (III), becomes established has proven advantageous.

An amount of water such that a proportion of the Lewis acid in the region of at most 60% by weight, preferably at most 35% by weight, particularly preferably at most 30% by weight, based on the total weight of phase (III), becomes established has proven advantageous.

Should the amount of water which is used for the extraction of the Lewis acid from the mixture (II) be such that the mixture (III) has a concentration of Lewis acid which is less than that of the fresh starting solution, the concentration of the Lewis acid may be increased by concentrating in a manner known per se, such as by preevaporation with removal of a proportion of the water from mixture (III), preferably to the concentration of Lewis acid that exists in the freshly used solution, advantageously at most 60% by weight, preferably at most 35% by weight, more preferably at most 32% by weight, especially preferably at most 30% by weight, and also advantageously at least 1% by weight, preferably at least 15% by weight, more preferably at least 25% by weight, based in each case on the total weight of Lewis acid in mixture (III).

Pure water can be employed in step b).

In a preferred embodiment, the water may comprise further constituents, such as ionic or nonionic, organic or inorganic compounds, in particular those which are homogeneously miscible with water to form a single phase or are dissolved in water.

In a particularly preferred embodiment, the addition of an inorganic or organic acid is possible. Preference is given to the use of acids which do not form an azeotrope with water and have a boiling point under the distillation conditions in step d) of the process according to the invention which is lower than that of the liquid diluent (V) or which form an azeotrope or heteroazeotrope with water under the distillation conditions in step d) of the process according to the invention.

Particular preference is given to hydrohalic acids, such as HF, HCl, HBr and HI, in particular HCl.

The amount of acid can advantageously be selected in such a way that the pH of the water employed in step b) is lower than 7.

The amount of acid can advantageously be selected in such a way that the pH of the water employed in step b) is greater than or equal to 0, preferably greater than or equal to 1.

Temperatures of at least 0° C., preferably at least 5° C., in particular at least 30° C., have proven advantageous for the reaction in step b).

Temperatures of at most 200° C., preferably at most 100° C., in particular at most 50° C., have proven advantageous for the reaction in step b).

This gives rise to pressures in the range from $10^{-3}$ to 10 MPa, preferably from $10^{-2}$ to 1 MPa, in particular from $5*10^{-2}$ to $5*10^{-1}$ MPa.

The optimum amount, pressure and temperature conditions for separation of the system into a phase (III) and a phase (IV) can easily be determined by means of a few simple preliminary experiments.

The phase separation can be carried out in a manner known per se in apparatuses described for such purposes, as disclosed, for example, in Ullmann's Encyclopedia of Industrial Chemistry, Vol. B3, 5th Edn., VCH Verlagsgesellschaft, Weinheim, 1988, pages 6–14 to 6–22.

The reaction in step b) can be carried out batchwise or preferably continuously, with a continuous countercurrent procedure, in particular in a multistage extraction column or a single-stage or multistage mixer/settler apparatus, having proven advantageous.

Phase (IV), which comprises the majority of the nitrile obtained in the hydrocyanation, can advantageously be sent for recovery of this nitrile.

In accordance with the invention, a liquid diluent (V) which c1) does not form an azeotrope with water and whose boiling point under certain pressure conditions is higher than that of water or c2) forms an azeotrope or heteroazeotrope with water under certain pressure conditions, is added to phase (III) in step c).

Diluents (V) should advantageously be selected in such a way that the said Lewis acid has a solubility of at least 0.1% by weight, based on the diluent (V), in the diluent (V) under the distillation conditions in step d).

Suitable diluents (V) are, for example, amides, in particular dialkylamides, such as dimethylformamide, dimethylacetamide, N,N-dimethylethyleneurea (DMEU), N,N-dimethylpropyleneurea (DMPU), hexamethylenephosphoramide (HMPT), ketones, sulfur-oxygen compounds, such as dimethyl sulfoxide, tetrahydrothiophene 1,1-dioxide, nitroaromatic compounds, such as nitrobenzene, nitroalkanes, such as nitromethane and nitroethane, ethers, such as diethers of diethylene glycol, for example diethylene glycol dimethyl ether, alkylene carbonates, such as ethylene carbonate, nitriles, such as acetonitrile, propionitrile, n-butyronitrile, n-valeronitrile, cyanocyclopropane, acrylonitrile, crotonitrile, allyl cyanide and pentenenitrile.

Diluents of this type can be employed alone or in the form of a mixture.

Aprotic, polar diluents of this type may comprise further diluents, preferably aromatic compounds, such as benzene, toluene, o-xylene, m-xylene or p-xylene, aliphatic compounds, in particular cycloaliphatic compounds, such as cyclohexane or methylcyclohexane, or mixtures thereof.

In a preferred embodiment, use can be made of diluents (V) which form an azeotrope or heteroazeotrope with water. The amount of diluent (V) relative to the amount of water in phase (III) is not crucial per se. It is advantageous to employ more liquid diluent (V) than corresponds to the amounts to be distilled off through the azeotropes in step d), so that excess diluent (V) remains as bottom product.

If a diluent (V) which does not form an azeotrope with water is employed, the amount of diluent relative to the amount of water in phase (III) is not crucial per se. In the case of a diluent (V) of this type, the diluent should preferably have a boiling point under the pressure and temperature conditions of the distillation in step d) of at least 5° C., in particular at least 20° C. and preferably at most 200° C., in particular at most 100° C., above that of water under these distillation conditions.

Organic diluents are advantageously suitable, preferably those having at least one nitrile group, in particular one nitrile group.

In a preferred embodiment, the nitrile employed can be a saturated aliphatic nitrile or an olefinically unsaturated aliphatic nitrile. Particularly suitable are nitriles having 3, 4, 5, 6, 7, 8, 9 or 10, in particular 4, carbon atoms, calculated without the nitrile groups, preferably the nitrile group.

In a particularly preferred embodiment, a suitable diluent (V) is one which partly or completely comprises, in particular consists of, the compound to be hydrocyanated in step e).

In an especially preferred embodiment, the diluent employed can be an olefinically unsaturated aliphatic mononitrile selected from the group consisting of 2-cis-pentenenitrile, 2-trans-pentenenitrile, 3-cis-pentenenitrile, 3-trans-pentenenitrile, 4-pentenenitrile, E-2-methyl-2-butenenitrile, Z-2-methyl-2-butenenitrile, 2-methyl-3-butenenitrile or a mixture thereof.

2-cis-Pentenenitrile, 2-trans-pentenenitrile, 3-cis-pentenenitrile, 3-trans-pentenenitrile, 4-pentenenitrile, E-2-methyl-2-butenenitrile, Z-2-methyl-2-butenenitrile, 2-methyl-3-butenenitrile and mixtures thereof are known and can be obtained by processes known per se, such as by hydrocyanation of butadiene in the presence of catalysts, for example as described in U.S. Pat. No. 3,496,215, or the linear pentenenitriles by isomerization of 2-methyl-3-butenenitrile as described in WO 97/23446 and processes described therein.

Particularly advantageous here are mixtures of the said pentenenitriles which comprise 2-cis-pentenenitrile, 2-trans-pentenenitrile or mixtures thereof mixed with 3-cis-pentenenitrile, 3-trans-pentenenitrile, 4-pentenenitrile, E-2-methyl-2-butenenitrile, Z-2-methyl-2-butenenitrile, 2-methyl-3-butenenitrile or mixtures thereof. In mixtures of this type, a reduction in the concentration of 2-cis-pentenenitrile, 2-trans-pentenenitrile, E-2-methyl-2-butenenitrile, Z-2-methyl-2-butenenitrile, 2-methyl-3-butenenitrile or mixtures thereof take place during the subsequent distillation in step d) of the process according to the invention since these form azeotropes with water which have a lower boiling point than the azeotropes of 3-cis-pentenenitrile, 3-trans-pentenenitrile, 4-pentenenitrile or mixtures thereof with water. In this embodiment, a mixture comprising 3-cis-pentenenitrile, 3-trans-pentenenitrile, 4-pentenenitrile or mixtures thereof and essentially anhydrous Lewis acid is obtained after the distillation as product (VII) of the process according to the invention.

This product can advantageously be employed for further hydrocyanation in the presence of a catalyst to give adiponitrile. A reduction in the concentration of 2-cis-pentenenitrile, 2-trans-pentenenitrile, E-2-methyl-2-butenenitrile, Z-2-methyl-2-butenenitrile or 2-methyl-3-butenenitrile is advantageous in as much as these two compounds undergo the said hydrocyanation to a considerably lesser extent than 3-cis-pentenenitrile, 3-trans-pentenenitrile, 4-pentenenitrile or mixtures thereof.

If the diluent employed is 2-cis-pentenenitrile, 2-trans-pentenenitrile, 3-cis-pentenenitrile, 3-trans-pentenenitrile, 4-pentenenitrile, E-2-methyl-2-butenenitrile, Z-2-methyl-2-butenenitrile, 2-methyl-3-butenenitrile or mixtures thereof, mixing ratios,of pentenenitrile to the said Lewis acid of at least 0.5 mol/mol, preferably at least 5 mol/mol, particularly preferably at least 15 mol/mol, have proven advantageous.

If the diluent employed is 2-cis-pentenenitrile, 2-trans-pentenenitrile, 3-cis-pentenenitrile, 3-trans-pentenenitrile, 4-pentenenitrile, E-2-methyl-2-butenenitrile, Z-2-methyl-2-butenenitrile, 2-methyl-3-butenenitrile or mixtures thereof, mixing ratios of pentenenitrile to the said Lewis acid of at most 10,000 mol/mol, preferably at most 5000 mol/mol, particularly preferably at most 2000 mol/mol, have proven advantageous.

Pentenenitriles of this type can advantageously be hydrocyanated to adiponitrile in step e).

In step d), the mixture of phase (III) and liquid diluent (V) is subjected to distillation under the pressure conditions mentioned in step c1) or c2) to give a mixture (VI) which has a higher content of water than of diluent (V) and a mixture (VII) which has a higher content of diluent (V) than of water, where mixture (VII) has a higher content of the said Lewis acid than does mixture (VI).

The pressure conditions for the distillation are not crucial per se. Pressures of at least $10^{-4}$ MPa, preferably at least $10^{-3}$ MPa, in particular at least $5*10^{-3}$ MPa, have proven advantageous.

Pressures of at most 1 MPa, preferably at most $5*10^{-1}$ MPa, in particular at most $1.5*10^{-1}$ MPa, have proven advantageous.

Depending on the pressure conditions and the composition of the mixture to be distilled, the distillation temperature then becomes established.

In the case of pentenenitrile as diluent, the distillation can advantageously be carried out at a pressure of at most 200 kPa, preferably at most 100 kPa, in particular at most 50 kPa.

In the case of pentenenitrile as diluent, the distillation can advantageously be carried out at a pressure of at least 1 kPa, preferably at least 5 kPa, particularly preferably at 10 kPa.

The distillation can advantageously be carried out by one-step evaporation, preferably by fractional distillation in one or more, such as 2 or 3, distillation apparatuses.

The distillation can be carried out in apparatuses which are conventional for this purpose, as described, for example, in Kirk-Othmer, Encyclopedia of Chemical Technology, 3rd Ed., Vol. 7, John Wiley & Sons, New York, 1979, pages 870–881, such as sieve-tray columns, bubble-tray columns, packed columns, columns with side take-off or dividing-wall columns.

The distillation can be carried out batchwise.

The distillation can be carried out continuously.

In the distillation in step d), mixture (VI) is usually obtained at the top. All or some of mixture (VI) can advantageously be fed back into step b), where it is reacted in accordance with the invention with mixture (II) as water or as a mixture with water.

If mixture (VI) is a single phase, all or some of mixture (VI) can be fed back.

If mixture (VI) is in the form of two phases, full or partial recycling of the phase having the higher water content by weight is advantageously possible.

Mixture (VII) is usually obtained as the bottom product in the distillation in step b). Mixture (VII) comprises the recovered fraction of the said Lewis acid and diluent (V); the water content of mixture (VII) should preferably be in the range from 0 to 0.5% by weight, in particular in the range from 0 to 50 ppm by weight, based on the total weight of mixture (VII).

In step e), mixture (VII) is fed to hydrocyanation of an olefinically unsaturated compound to give a nitrile which has a miscibility gap with water under certain amount, pressure and temperature conditions, in the presence of a catalyst system comprising a Lewis acid and a complex compound comprising a phosphorus-containing compound which is suitable as ligand and a central atom which is suitable for this compound.

The complex compound employed here can advantageously be the complex compound separated off in step a).

The olefinically unsaturated compound to be hydrocyanated is preferably diluent (V).

EXAMPLES

The % by weight or ppm by weight data given in the examples are based, unless stated otherwise, on the total weight of the respective mixture.

The Zn or zinc chloride content was determined by atomic emission spectrometry.

The chlorine content was determined by the Schoeniger method.

The water concentration was determined potentiometrically by titration by the Karl-Fischer method.

Example 1

In a continuously operated vacuum distillation column with metal mesh packing (type CY, Sulzer Chemtech, internal diameter Ø=50 mm, height 130 cm) with a thin-film evaporator as heat exchanger at the column bottom, a condenser operated at 30° C. at the top and a phase separation vessel cooled to 0° C. in the reflux, 240 g/h of a solution of 30% by weight of zinc chloride in trans-3-pentenenitrile having a water content of 0.4% by weight were metered into the distillation column above the mesh packing. At a pressure of p=10 kPa (absolute), a two-phase mixture was obtained as condenser distillate at 344 K. The upper phase, essentially consisting of trans-3-pentenenitrile, was fed back continuously to the top of the column. The lower phase essentially consisted of water and was continuously pumped out of the phase separation vessel. A homogeneous solution of $ZnCl_2$ in trans-3-pentenenitrile was separated off at 348 K at the bottom of the column. The water content in the bottom product had dropped to 76 ppm by weight of $H_2O$ after a distillation run time of 17 hours and to 50 ppm by weight after 41 hours.

Example 2

1 kg of trans-3-pentenenitrile and 500 g of water were added to 4 kg of the bottom product obtained in Example 1. The homogeneous mixture was metered into the distillation column operated as in Example 1 at a metering rate of 206 g/h.

After continuous operation for 24 hours, the bottom product comprised 350 ppm by weight of water, 16.9% by weight of chlorine, calculated as Cl, and 15.5% by weight of Zn, in each case based on the total weight of the solution; an experimentally found Cl:Zn ratio of 2.01 can be derived therefrom.

Gas-chromatographic analysis by derivatization with MSTFA (2,2,2-trifluoro-N-methyl-N-(trimethylsilyl)acetamide) showed no detectable quantities of the saponification product 3-pentenoic acid.

Analysis for polymeric degradation products by gel permeation chromatography showed no detectable quantities of polymeric product.

The zinc chloride solution in 3-pentenenitrile obtained in this way can be employed in the hydrocyanation of 3-pentenenitrile in the presence of nickel(0) phosphite catalysts and shows no difference in activity compared with a solution freshly prepared from 3-pentenenitrile and anhydrous zinc chloride.

Example 3

In a continuously operated countercurrent extraction column (internal diameter Ø=30 mm, 50 cm deep bed of Raschig rings), 110 g/h of a solution of 0.52% by weight of $ZnCl_2$ in a mixture of 20% by weight of trans-3-pentenenitrile and the remainder of adiponitrile were metered into the lower part of the extraction column. 170 g/h of water were metered into the upper part. After continuous operation for more than 3 hours, the extracted organic phase with less than 10 ppm by weight of Zn was obtained at the upper end of the extraction column. The aqueous phase with 0.30% by weight of $ZnCl_2$ was obtained at the lower end of the extraction column.

Example 4

In a continuously operated mixer/settler apparatus consisting of a tank with a capacity of 2 l which was operated at room temperature and was fitted with an inclined-blade stirrer operated at 700 rpm and a hydrostatic overflow into a downstream phase separator with a capacity of 0.5 l, 320 g/h of a solution of 0.52% by weight of $ZnCl_2$ in a mixture of 20% by weight of trans-3-pentenenitrile and the remainder of adiponitrile as well as 100 g/h of water were metered in. After operation for 7 hours, the organic phase with 30 ppm of Zn was obtained via the phase separator, and the separated-off aqueous phase comprised 0.75% by weight of Zn. An accumulation of solid which accumulated at the phase interface was observed in the phase separator after a short operating time. According to analysis by X-ray diffraction, the solid consisted of $ZnCl_2.Zn(OH)_2.2H_2O$.

Example 5

A mixture of 500 g of an aqueous zinc chloride solution obtained by extraction as described in Example 3 and 540 g of an aqueous zinc chloride solution obtained as described in Example 4 and comprising 0.94% by weight of $ZnCl_2$ and having a pH of 6 was metered into the distillation column operated as described in Example 1 at a metering rate of 80 g/h. 320 g/h of trans-3-pentenenitrile were metered into the distillation column by means of a second pump. After continuous distillation for 9.5 hours, 310 ppm by weight of water and 0.10% by weight of Zn (corresponding to 0.20% by weight of $ZnCl_2$) were found in the bottom product.

Example 6

320 g/h of a solution of 0.52% by weight of $ZnCl_2$ in a mixture of 20% by weight of trans-3-pentenenitrile and the remainder of adiponitrile, as well as 100 g/h of a 0.1 N solution of HCl in water having a pH of 1 were metered into a mixer/settler apparatus operated as described in Example 4. After operation for 7 hours, the organic phase comprising 85 ppm of Zn was obtained via the phase separator, and the separated-off aqueous phase comprised 1.88% by weight of Zn. In contrast to Example 4, no solid was observed in the phase separator.

Example 7

A mixture of 190 g of an aqueous zinc chloride solution obtained by extraction as described in Example 3, 370 g of an aqueous zinc chloride solution obtained as described in Example 4, and 430 g of an aqueous zinc chloride solution which was obtained as described in Example 4 and which comprised 0.72% by weight of Zn and had a pH of 1 was metered at a metering rate of 80 g/h into the distillation column operated as described in Example 1. 320 g/h of trans-3-pentenenitrile were metered into the distillation column by means of a second pump. After continuous distillation for 9.5 hours, 210 ppm by weight of water and 0.18% by weight of Zn were found in the bottom product. The aqueous phase which was obtained at the phase separator at the top of the column had a pH of 1.

The solution of $ZnCl_2$ in trans-3-pentenenitrile obtained at the bottom of the column can be hydrocyanated to adiponitrile in the presence of Ni(0) phosphite catalysts.

We claim:

1. A process for the recovery of a Lewis acid from a reaction mixture (I) which has been obtained in the hydrocyanation of an olefinically unsaturated compound to a nitrile which has a miscibility gap with water under certain pressure and temperature conditions, in the presence of a catalyst system comprising a Lewis acid and a complex compound comprising a phosphorus-containing compound which is suitable as ligand and a central atom which is suitable for the complex compound, which comprises a) removing the complex compound from mixture (I) to give a mixture (II), b) adding water to the mixture (II) and placing the mixture (II) under pressure and temperature conditions such that a phase (III) which has a higher content of water than of the nitrile and a phase (IV) which has a higher content of the nitrile than of water are obtained, where phase (III) has a higher content of the Lewis acid than does phase (IV), c) adding a liquid diluent (V) that c1) does not form an azeotrope with water and whose boiling point under certain pressure conditions is higher than that of water, or c2) forms an azeotrope or heteroazeotrope with water under certain pressure conditions, to phase (III) to form a mixture of phase III and liquid diluent V, d) subjecting the mixture of phase (III) and liquid diluent (V) to distillation under the pressure conditions of step c1 or step c2, giving a mixture (VI) which has a higher content of water than of the diluent (V) and a mixture (VII) which has a higher content of the diluent (V) than of water, where the mixture (VII) has a higher content of the Lewis acid than does the mixture (VI), and e) subjecting the mixture (VII) to hydrocyanation of the olefinically unsaturated compound to give the nitrile, in the presence of the catalyst system.

2. A process as claimed in claim 1, where the mixture (VII) has a water content of less than 0.5% by weight.

3. A process as claimed in claim 1, where the solubility of the Lewis acid in the diluent (V) under the distillation conditions of step d is at least 0.1% by weight.

4. A process as claimed in claim 1, where step b is carried out in countercurrent in a multistage extraction column.

5. A process as claimed in claim 1, where all or some of the mixture (VI) is fed back into step b.

6. A process as claimed in claim 1, where the water used in step b has a pH of less than 7.

7. A process as claimed in claim 1, where the water used in step b has a pH in the range from 0 to less than 7.

8. A process as claimed in claim 1, where an acid is added to the water used in step b.

9. A process as claimed in claim 8, where HCl is added to the water.

10. A process as claimed in claim 1, where the diluent (V) contains all or some of the unsaturated compound to be hydrocyanated in step e.

11. A process as claimed in claim 1, where the diluent (V) is a nitrile selected from the group consisting of 2-cis-pentenenitrile, 2-trans-pentenenitrile, 3-cis-pentenenitrile, 3-trans-pentenenitrile, 4-pentenenitrile, E-2-methyl-2-butenenitrile, Z-2-methyl-2butenenitrile, 2-methyl-3-butenenitrile or a mixture thereof.

12. A process as claimed in claim 1, where all or some of undissolved constituents are separated off from the mixture (II) between steps a and b or between steps b and c.

13. A process as claimed in claim 11, where the solubility of the Lewis acid in the diluent (V) under the distillation conditions of step d is at least 0.1% by weight.

14. A process as claimed in claim 11, where an acid is added to the water used in step b.

15. A process as claimed in claim 11, where the water used in step b has a pH of less than 7.

16. A process as claimed in claim 11, where step b is carried out in countercurrent in a multistage extraction column.

17. A process as claimed in claim 11, where the mixture (VII) has a water content of less than 0.5% by weight.

18. A process as claimed in claim 17, where all or some of the mixture (VI) is fed back into step b.

* * * * *